United States Patent [19]
Howell et al.

[11] Patent Number: 5,770,430
[45] Date of Patent: Jun. 23, 1998

[54] CELLULAR INJURY RESPONSE ELEMENT AND USES THEREOF

[75] Inventors: Stephen B. Howell, Del Mar, Calif.; Dennis P. Gately, Philadelphia, Pa.

[73] Assignee: Research Development Foundation, Carson City, Nebr.

[21] Appl. No.: 661,649

[22] Filed: Jun. 11, 1996

[51] Int. Cl.⁶ .............................. C12N 5/00; C12N 15/63; C07H 21/04

[52] U.S. Cl. ................................. 435/240.2; 435/320.1; 536/23.1; 536/24.1

[58] Field of Search ...................... 424/93.21; 435/91.1, 435/240.1, 243, 252.3, 320.1; 514/44; 536/22.1, 23.1, 24.1

[56] References Cited

PUBLICATIONS

Fawcett et. al.. Physical and functional association between GADD153 and CCAAT–enhancer–binding proteinbeta during cellular stress. J. Biol. Chem. vol.271(24):14285–14289, Jun. 15, 1996.

Sylvester et. al.. Induction of GADD153, a CCAAT/enhancer binding protein (C/EBP)–related gene, during the acute phase response in rats. J. Biol. Chem.. vol. 269(31):20119–20125, Aug. 5, 1994.

*Primary Examiner*—David Guzo
*Assistant Examiner*—William Sandals
*Attorney, Agent, or Firm*—Benjamin Aaron Adler

[57] ABSTRACT

The present invention provides a vector with a DNA sequence coding for a cellular injury element promoter from nucleotides –74 to –35 of the GADD153 promoter, relative to the start of transcription. The vector includes an origin of replication in operable linkage with a DNA sequence coding for the promoter. Also, a host cell is transfected with the vector and expresses the cellular injury response element promoter.

16 Claims, 8 Drawing Sheets

Figure 2

| Construct | Fold Induction ± SD |
|---|---|
| -786 ——————————ᵀᴬᵀᴬ[Luciferase] | 9.3 ± 0.4 |
| -336 ——————ᵀᴬᵀᴬ[Luciferase] | 9.1 ± 1.1 |
| -247 ————————ᵀᴬᵀᴬ[Luciferase] | 9.9 ± 0.3 |
| -85 ———ᵀᴬᵀᴬ[Luciferase] | 9.5 ± 1.1 |
| -74 ——ᵀᴬᵀᴬ[Luciferase] | 20.0 ± 3.3 |
| -74 Sp1 –x–ᵀᴬᵀᴬ[Luciferase] Mutant | 5.3 ± 2.3 |
| -35 ᵀᴬᵀᴬ[Luciferase] | 2.2 ± 0.2 |

```
AGGCTCCTGGGTCCCGCCCCCCaaaagaggg  Wild Type
tccgaggacccaGGGCGGGGGGTTTTCTccc

AGGCTCCTGGGTCCCTAGACCCaaaagaggg  Sp1 Mutant
tccgaggacccaGGGATCTGGGTTTTCTccc

AGGCTCCTGGGTCCCGCCCCCCtctctaggg  3' Mutant
tccgaggacccaGGGCGGGGGGAGAGATccc
```

CELLULAR INJURY RESPONSE ELEMENT AND USES THEREOF

BACKGROUND OF THE INVENTION

1. Field of the Invention

The present invention relates generally to the fields of molecular biology and the pharmacology of cancer chemotherapeutics. More specifically, the present invention relates to a novel cellular injury response element and uses thereof.

2. Description of the Related Art

Treatment of mammalian cells with genotoxic agents causes an increase in the mRNA levels of a number of "damage response" genes (reviewed by Holbrook and Fornace (1)). Many of these genes are also inducible by phorbol ester treatment. Among those that do not respond to phorbol ester treatment, some can be activated by the tumor suppressor gene p53, such as WAF1 and GADD45 (2,3). However, there are also a number of DNA damage inducible genes for which the activation signal is unknown, and GADD153 is one of these genes. GADD153 is of particular interest because the magnitude of the increase in GADD153 mRNA following cellular injury is greater than most other "damage response" genes.

GADD153 was originally cloned by subtractive hybridization of UV-treated versus proliferating Chinese hamster ovary cells. The GADD153 gene was one of a subset of genes that was induced by UV-radiation and other forms of DNA damage, but not by heatshock or phorbol ester treatment (4). This subset of genes was found to be coordinately regulated by a number of agents that damage DNA or induce cell cycle arrest (5). The human homolog has now been cloned and localized to the 12q13.1-q13.2 region on chromosome 12 (6). This gene is highly conserved, the human gene showing 78% nucleotide identity with the hamster gene.

The role of the GADD153 gene product has not been well defined, but there is some evidence that it plays a role in cell cycle control during the cellular injury response. When transfected into cells under the control of a constitutively active promoter, GADD153 expression blocks the ability of human ovarian carcinoma cells to proliferate and form colonies. Zhan et al. reported that co-transfection of a GADD153-expressing vector with a vector containing a selectable neomycin resistance gene decreased the plating efficiency of H1299 and HeLa cells to 30% of that obtained with the neomycin plasmid alone (7). Barone et al. microinjected an expression vector containing the GADD153 coding region, or purified GADD153 protein into cells (8). Both the plasmid and the purified protein prevented the cells from exiting $G_1$ and entering the next S phase as measured by bromodeoxyuridine incorporation. These results argue that the GADD153 gene product may be involved in cellular machinery that causes arrest at the $G_1/S$ boundary after DNA damage or other kinds of cellular injury.

It has been previously demonstrated in cell lines and xenografts that the magnitude of the increase in GADD153 message is closely linked to the extent of cellular injury caused by the chemotherapeutic drugs cisplatin and paclitaxel, and that these two agents transcriptionally activate the GADD153 promoter via different signal transduction pathways (9). As an initial step towards defining these pathways in more detail, the GADD153 promoter must be dissected to identify the components essential to the transcriptional activation produced by paclitaxel.

The prior art is deficient in the lack of the identification and characterization of a cellular injury response element (CIRE) that is required for the paclitaxel activation of the GADD153 promoter. The present invention fulfills this longstanding need and desire in the art.

SUMMARY OF THE INVENTION

The GADD153 promoter is transcriptionally activated by paclitaxel-induced injury. Promoter deletion from −786 to −85 basepairs relative to the start of transcription had no significant effect on activation, but deletion to the TATA box abolished it. Placement of the 39 bases from −74 to the TATA box (cellular injury response element; CIRE) upstream of the adenovirus E4 TATA box conferred paclitaxel inducibility. The only currently recognized consensus sequence present in the cellular injury response element is an Sp1 site; mutation of this site inhibited paclitaxel activation. Paclitaxel failed to activate a SV40-driven luciferase construct containing 5 Sp1 sequences, and Sp1 sites further upstream in the GADD153 promoter were not essential for activation. Pure Sp1 and nuclear extracts from uninjured and paclitaxel-injured cells protected the same region from −62 to −48 bases on the non-coding strand and −74 to −53 on the coding strand. Nuclear extracts shifted the cellular injury response element to the same extent as purified Sp1, but had no effect on a cellular injury response element with a mutated Sp1 site in gel shift assays. Immunodepletion of Sp1 abolished the shift; antibody to Sp1 produced a supershift. These data indate that paclitaxel activates the GADD153 promoter through a constitutively occupied Sp1 site at −61 bases.

The present invention demonstrates that a short 39 basepair sequence of DNA that functions as an inducible promoter in human cells and tissues has been identified. This promoter is markedly activated by certain types of cellular injury, including the type of injury produced by cancer chemotherapeutic agents and UV irradiation. This sequence has been identified as a cellular injury responsive element (CIRE). This DNA fragment when coupled to a reporter gene can be used, inter alia, to detect and quantitate the extent of cellular injury in in vitro test systems.

The minimum size of the sequence required for activation by cellular injury has been established, as well as the requirement for an intact Sp1 binding site within the cellular injury responsive element. Studies in animal models have been completed showing that the full length GADD153 promoter, of which the cellular injury responsive element is the key functional element, can be used to quantitate the extent of cellular injury in vivo. In addition, a clinical trial has been completed demonstrating that the extent of induction of the GADD153 promoter predicts clinical response in patients with head and neck carcinoma.

The knowledge of the Cellular Injury Responsive Element can be used as the basis for the development of diagnostic strategies relevant to the treatment of cancer patients and to the broad field of gene therapy. Possible applications include but are not limited to the following. The Cellular Injury Responsive Element can be used to identify and guide the development of new anticancer drugs. Cells transiently or permanently transfected with a construct containing the Cellular Injury Responsive Element linked to a reporter gene can be used for high throughput screening of natural products and novel classes of drugs as well as analogs of existing drugs. Representative examples of such reporter genes are known to those having ordinary skill in this art.

The Cellular Injury Responsive Element can be used to screen for cellular toxicity of drugs. Cells transiently or permanently transfected with a construct containing the Cellular Injury Responsive Element linked to a reporter gene could be used for high throughput screening to eliminate drugs that cause cellular injury.

The Cellular Injury Responsive Element can be used to activate genes that serve to help cells recover from injury. Genes are known that, when expressed, can help prevent death in an injured cell. Using currently available gene therapy techniques, the Cellular Injury Responsive Element can be coupled to such a protective gene and inserted into normal tissues (e.g., bone marrow) to help protect against such injurious agents as cancer chemotherapeutic drugs or radiation therapy. Representative examples of such protective genes include insulin, G-CSF, or thrombopoeitin.

The Cellular Injury Responsive Element can be used to amplify the injury signal and cause cells to die after only slight injury. If the Cellular Injury Responsive Element were coupled to a toxin gene, then even very slight injuries could cause the cell to die. This could be used as part of a gene therapy approach to the treatment of cancer which would involve inserting the Cellular Injury Responsive Element-toxin gene construct into the malignant cells to amplify whatever injury could be achieved using conventional chemotherapeutic or radiation therapeutic approaches. Representative examples of such toxin genes include gelonin, ricin, and saponin as well as others known to those of ordinary skill in this art.

In one embodiment of the present invention, there is provided a vector comprising a DNA sequence coding for a cellular injury response element promoter, said promoter comprising nucleotides −74 to −35 of the GADD153 promoter, relative to the start of transcription, said vector is capable of replication in a host which comprises, in operable linkage:

a) an origin of replication;
b) a promoter; and
c) a DNA sequence coding for said promoter.

In another embodiment of the present invention, there is provided a host cell transfected with the vector of the present invention, said vector expressing a cellular injury response element promoter, said promoter comprising nucleotides −74 to −35 of the GADD153 promoter, relative to the start of transcription.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows the effect of deletion mutations on the paclitaxel activation of the GADD153 promoter. Deletions in the GADD153 promoter of pGADD-LUC were created by a PCR-based method and lipofected into the 2008 cells. The cells were treated with 70 nM paclitaxel and luciferase activity was measured 24 hours after treatment. The Sp1 mutation was created by substituting CCTAGA for the wild type CCGCCC. Each data point represents the mean of at least three experiments performed in duplicate ± SD.

DETAILED DESCRIPTION OF THE INVENTION

Figure 1:
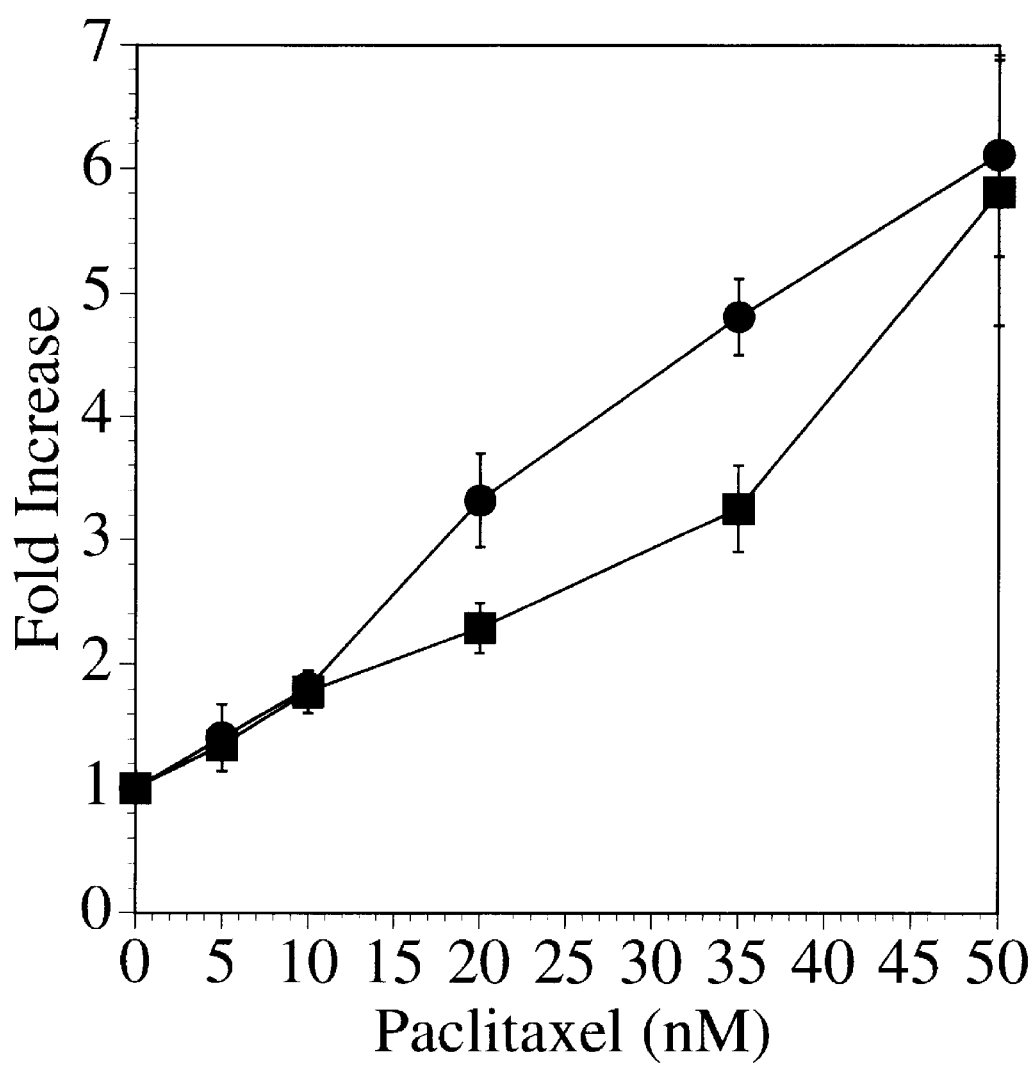
FIG. 1 shows the relative increase in GADD153 promoter activity and endogenous mRNA levels after paclitaxel treatment. Cells were lipofected with pGADD-LUC, treated with paclitaxel and luciferase activity (circles, 1) or endogenous GADD153 mRNA levels, (squares, n) were measured after 24 hours. Each data point represents the mean of two experiments performed in duplicate ±SEM.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acid described herein are preferred to be in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomeclature, *J Biol. Chem.*, 243:3552–59 (1969), abbreviations for amino acid residues are shown in the following Table of Correspondence:

TABLE OF CORRESPONDENCE

| SYMBOL 1-Letter | 3-Letter | AMINO ACID |
| --- | --- | --- |
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxyterminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an automous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding complexes of proteins that serve to initiate transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase and proteins required for assembly of the transcription initiation complex. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the other domains of the polypeptide, that communicates to the host cell to direct the polypeptide to the cell surface or cause the polypeptide to be secreted into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or a common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous' region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, florescein, rhodamine, auramine, Texas Red, AMCA blue and Lucifer Yellow. A particular detecting material is anti-rabbit antibody prepared in goats and conjugated with fluorescein through an isothiocyanate.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, $\beta$-glucuronidase, $\beta$-D-glucosidase, $\beta$-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

Thus, the present invention is directed to a vector comprising a DNA sequence coding for a cellular injury response element promoter, said promoter comprising nucleotides −74 to −35 of the GADD153 promoter, relative to the start of transcription, said vector is capable of replication in a host which comprises, in operable linkage: (a) an origin of replication; (b) a promoter; and (c) a DNA sequence coding for said promoter. Preferably, the vector is selected from the group consisting of a retroviral vector, an adenoviral vector, an adeno-associated vector and a plasmid. Specifically, the vector contains the promoter having the sequence shown in SEQ ID No. 9.

The present invention is also directed to a host cell transfected with the vector of claim 1, said vector expressing a cellular injury response element promoter, said promoter comprising nucleotides −74 to −35 of the GADD153 promoter, relative to the start of transcription. Preferably, the host cell is selected from group consisting of bacterial cells, mammalian cells and insect cells.

The novel CIRE of the present invention may be used to activate the expression of genes coding for a secreted hormone, gorwth factor, cytokine, chemokine or other polypeptide. For example, one may insert a vector into cells in the body that contained the CIRE driving a gene whose product was a protein of interest (for example insulin, G-CSF or thrombopoeitin). One could then regulate the amount of the protein being produced and released to the rest of the body by slightly injuring the cells containing the inserted vector with local hyperthermia, irradiation (UV, microwave, gamma), or possibly even mechanical trauma.

In a separate method, the CIRE of the present invention may be used to activate the expression of genes whose products are transcription factors or other proteins capable of regulating the expression of other genes, families of genes, differentiation pathways or metabolic pathways. Thus, the CIRE could be used to turn on the expression of regulatory proteins capable of modulating the activity of a whole group of genes or a whole pathway. The mechanism of turning the CIRE on would be the same as outlined above (heat, radiation, etc.. In this embodiment, one could activate a (1) biosynthetic pathway, e.g., to produce more of a steroid molecule or (2) a degradation pathway, e.g., to metabolize a toxin building up in the body. Furthermore, the CIRE may be used to turn on the expression of a transcription factor that could cause the cell to proliferate (e.g., E2F-1 or myc). This would permit external control of the proliferation rate of a population of cells placed back in the body after insertion of the CIRE-gene construct.

Another embodiment of the present invention would be to use the CIRE to turn on the synthesis of the rate limiting enzyme in the melanin synthesis pathway such that whenever the cell was exposed to UV radiation (sunburn) it automatically protected itself by turning on melanin synthesis.

In yet another embodiment of the present invention, the CIRE can be used to turn on the expression of genes that code for cell surface and intracellular receptors. The CIRE would be coupled to a gene for a receptor so that when the cell was slightly injured, it expressed the receptor and now became responsive to hormones, growth factors, etc. already in its environment. This would be an alternative approach to controlling cell proliferation. For example, if one turned on the expression of the receptor for VEGF, one could get the cell to proliferate at sites of new blood vessel formation. If one turned on the expression of a steroid receptor gene, one might now be able to get the cell to respond to glucocorticoids, etc.

The following examples are given for the purpose of illustrating various embodiments of the invention and are not meant to limit the present invention in any fashion.

EXAMPLE 1

Chemicals

Paclitaxel was obtained from Calbiochem (San Diego, Calif.). Luciferin was obtained from Analytical Luminescence (San Diego, Calif.). DNAse I was obtained from Sigma (St. Louis, Mo.).

EXAMPLE 2

Cell Culture

The human ovarian carcinoma cell line 2008 (10) was carried as an exponentially growing monolayer in a humidified incubator at 37° C. and 5% $CO_2$ in RPMI 1640 supplemented with 5% fetal calf serum and 2 mM glutamine.

EXAMPLE 3

Vector Construction pGADD-LUC, a GADD153 promoter driven luciferase reporter construct was created by ligating the Cla I/Hind III fragment of p9000 (gift of Dr. N. J. Holbrook, NIA, NIH, Baltimore, Md.) containing the hamster GADD153 promoter into the Acc I/Hind III site of pB-LUC (11). pB-LUC contains the firefly luciferase gene ligated into the BamHI site of pBluescript KS⁻ (gift of Dr. Linda Quattrochi). Delection mutations were made using a PCR based strategy. Primers containg Xho I linders and an antisense primer within the multicloning region of pBluescript were used to generate deletion fragments of the promoter. These fragments were cut with Xho I and Hind III and ligated into the Xho I/Hind III sites of p-BLUC. Mutations in the Sp1 binding site were made by substituting TCC TAG ACC for TCC CGC CCC at position −59 relative to the start of transcription. Linker scanning mutations were made using primers containing the Sp1 mutation (as above), or 3' mutation (substituting CCT CTC TAG for CCA AAA GAG at position −61 relative to the start of transcription) in both the sense and antisense orientation. Fragments were made from the mutation to the pBluescript cloning region and from the mutation to −185 (with Xho I linker) relative to the start of transcription. These fragments were mixed and used as template for a reaction with primers from −185 (with Xho I linker) to the pBluescript cloning region. These fragments were cut with Xho I and Hind III and ligated into the Xho I/Hind III sites of pB-LUC.

EXAMPLE 4

Luciferase Assay

The cells were transfected with the pGADD-LUC contruct by a modification of the method described by Rose et al. (12). Cells were plated at $3 \times 10^5$ cells per 35 mm dish, and then 18 hours later they were incubated at 37° C. with 5 µg plasmid DNA and 30 µl liposomes in 1 ml RPMI 1640. After 3 hours the lipids were removed and the cells were treated with paclitaxel for 24 hours. The cells were lysed in 100–500 µl of lysis buffer (25 mM glycylglycine pH 7.8, 15 mM $MgSO_4$, 4 mM EGTA, 1% Triton X-100, 1 mM dithiothreitol). Luciferase activity was measured by a modification of the method described by Brasier et al. (13). Fifty µl of cell lysate was added to 200 µl of reaction buffer (lysis buffer with 15 mM potassium phosphate pH 7.8, and 2 mM ATP added). Light emission was measured after injection of 100 µl of 1 mM luciferin into the lysate/reaction mixture using a MonoLight 2001 (Analytical Luminescence, San Diego, Calif.).

EXAMPLE 5

Nuclear Protein Extraction

Nuclear extracts were made by pelleting $10^8$ cells and resuspending in Buffer A (10 mM HEPES, pH 7.9, 1.5 mM $MgCl_2$, 10 mM KCl, & 1 mM DTT). Cells were allowed to equilibrate for 10 minutes on ice and were collected by centrifugation for 5 minutes at 500×g. Cells were lysed in Buffer B (Buffer A with 0.2% Nonidet P-40, 1 mM PMSF, 10 μg/ml leupeptin and 10 μg/ml aprotinin) for 10 minutes on ice. Nuclei were collected by centrifucation for 10 minutes at 1000×g. Nuclei were suspended in Buffer C (20 mM HEPES, pH 7.9, 20% glycerol, 100 mM KCl, 0.2 mM EDTA, 1 mM dithiotheritol, 1 mM phenylmethylsulfonyl fluoride, 10 μg/ml leupeptin and 10 μg/ml aprotinin) and then lysed by bringing the final KCl concentration to 0.4 M and rocking for 30 minutes at 4° C. Genomic DNA was pelleted by centrifugation for 40 minutes at 65,000 RPM (175,000×g) in a Beckman table-top ultracentrifuge. The supernatant containing the nuclear proteins was recovered and glycerol was added to a final concentration of 40%. Sp1 was immunodepleted from extracts by incubation for 1 hour at 4° C. with a rabbit polyclonal antibody raised against amino acids 520–538 of the human Sp1 protein (PEP2, Santa Cruz Biotechnology, Inc., Santa Cruz, Calif.). The lysate was cleared using protein A/sepharose (Sigma, St. Louis, Mo.).

EXAMPLE 6

DNAse I footprinting

A fragment of DNA corresponding to bases −185 to +21 relative to the start of transcription was generated by PCR. The fragment was cut with either Xho I or Eco RV to remove one of the primers, and the DNA was $^{32}$P-labeled on a single strand by T4 polynucleotide kinase (Promega, Madison, Wis.), precipitated to remove unincorporated nucleotide, and resuspended. Ten μg of nuclear extract, 2 footprinting units of purified Sp1 (Promega, Madison, Wis.), or no protein controls were diluted to 25 μl with buffer Z (25 mM HEPES, pH 7.5, 100 mM KCl, 12.5 mM $MgCl_2$, 10 μM $ZnSO_4$, 20% glycerol, & 0.1% Nonidet P-40). Twenty-five μl of a solution containing 10 μl 10% polyvinyl alcohol (Sigma, St. Louis, Mo.), 1 mg poly dI/dC, and ≧10,000 cpm (10–25 fmol) labeled DNA was added to the protein mixture and incubated 15 minutes at room temperature. Fifty μl of 5 mM $CaCl_2$/10 $MgCl_2$ mix was added and incubated for 1 minute. Two μl of DNAse I (Sigma, 10 mg/ml, dilutions ranging from 1:2000 to 1:100,000) was then added and incubated for another minute. The reaction was stopped by adding 90 μl of stop solution (20 mM EDTA, pH 8.0, 1% SDS, 0.2 M NaCl, 250 μg/ml glycogen). Proteins were digested with 5 μl of 10 mg/ml proteinase K and removed by phenol extraction. The DNA was precipitated and resuspended in 3 μl formamide loading buffer. The bands were separated on a 6% polyacrylamide/urea sequencing gel, dried and expeosed to Biomax MS film. Sequencing was done with the Promega Femptomole sequencing kit (Promega, Madison, Wis.) using the protocol for end-labeled primers.

EXAMPLE 7

Gel Mobility Shift Assays

Oligonucleotides corresponding to the cellular injury response element were constructed at the University of California, San Diego Molecular Biology Core facility and annealed together by heating for 5 minutes at 65° C. and incubating overnight at 37° C. in 10 mM Tris, pH 7.8, 0.1 M NaCl and 1 mM EDTA. The doublestranded cellular injury response element (or Sp1 mutated cellular injury response element) was ethanol precipitated, resuspended in $H_2O$ and $^{32}$P endlabeled with T4 polynucleotide kinase (Promega, Madison, Wis.), precipitated to remove unincorporated nucleotide, and resuspended to 500 pg/μl (approximately 50,000 CPM/μl).

50,000 CPM of the cellular injury response element, 1 μg poly dI/dC, 10 μg nuclear extract or 2 footprinting units of human Sp1 protein (Promega, Madison, Wis.) were suspended in 12.5 mM HEPES, pH 7.8, 50 mM KCl, 6.25 mM $MgCl_2$, 5 μM $ZnSO_4$, 10% glycerol, and 0.05% Nonidet P-40 and incubated for 30 minutes at room temperature. The bands were separated on a 4% polyacrylamide/0.5 X TBE (45 mM Tris-borate, 10 mM EDTA) gel, dried and were visualized using the Molecular Imager System (Bio-Rad, Hercules, Calif.). Supershift assays were performed as above with the addition of 0.05 g anti-Sp1 antibody (PEP2, Santa Cruz Biotechnology, Inc.) or non-specific rabbit antibody to the reaction mixture after the 30 minute incubation and incubating for an additional 30 minutes.

EXAMPLE 8

Northern Blotting

Total cellular RNA was extracted and Northern blots prepared using MagnaGraph nylon membranes (MSI, Westboro, Mass.) by standard techniques (14). The extent of hybridization was quantitated by the Molecular Imager System (Bio-Rad, Hercules, Calif.). The human GADD153 probe was obtained from Dr. J. J. Holbrook (NIA, NIH, Baltimore, Md.). Lane loading differences were corrected for by comparison to the same blot hybridized with a β-actin probe.

EXAMPLE 9

Effect of paclitaxel on the GADD153 promoter and endogenous GADD153 mRNA

The effect of paclitaxel on the GADD153 promoter driven luciferase construct and endogenous GADD153 mRNA was studied in the 2008 ovarian carcinoma cell line. Cells were transfected with 5 μg pGADD-LUC and then expeosed to paclitaxel for 24 hours at which point luciferase activity and endogeous GADD153 mRNA levels were determined. As shown in FIG. 1, paclitaxel induced a concentration-dependent increase in both GADD153 promoter activity and endogenous GADD153 message level that were of the same order of magnitude.

Deletions in the GADD153 promoter were created by PCR and are shown in FIG. 2. These constructs were transfected into 2008 cells and tested for inducibility following exposure to 70 nM paclitaxel relative to cells treated with vehicle alone. Deletions from −786 to −85 relative to the start of transcription had no significant effect on the activation of the GADD153 promoter by paclitaxel. Deletion to −74 base pairs increased the inducibility almost 2-fold, suggesting that the 11 bases 5' of −74 contain a transcriptional repressor. Further deletion of the promoter to −35 bases (leaving only the TATA box) decreased the paclitaxel inducibility to 2.2-fold. This suggests that the 39 basepairs from −74 to the TATA box contain an element which is responsible for the paclitaxel-induced increase in GADD153 promoter activity. The finding that the construct containing only the TATA box is activated 2-fold suggests that paclitaxel-induced injury has a slight positive effect on the basal transcription machinery.

EXAMPLE 10

Transfer of the Paclitaxel-responsive element to a heterologous promoter

Figure 3:
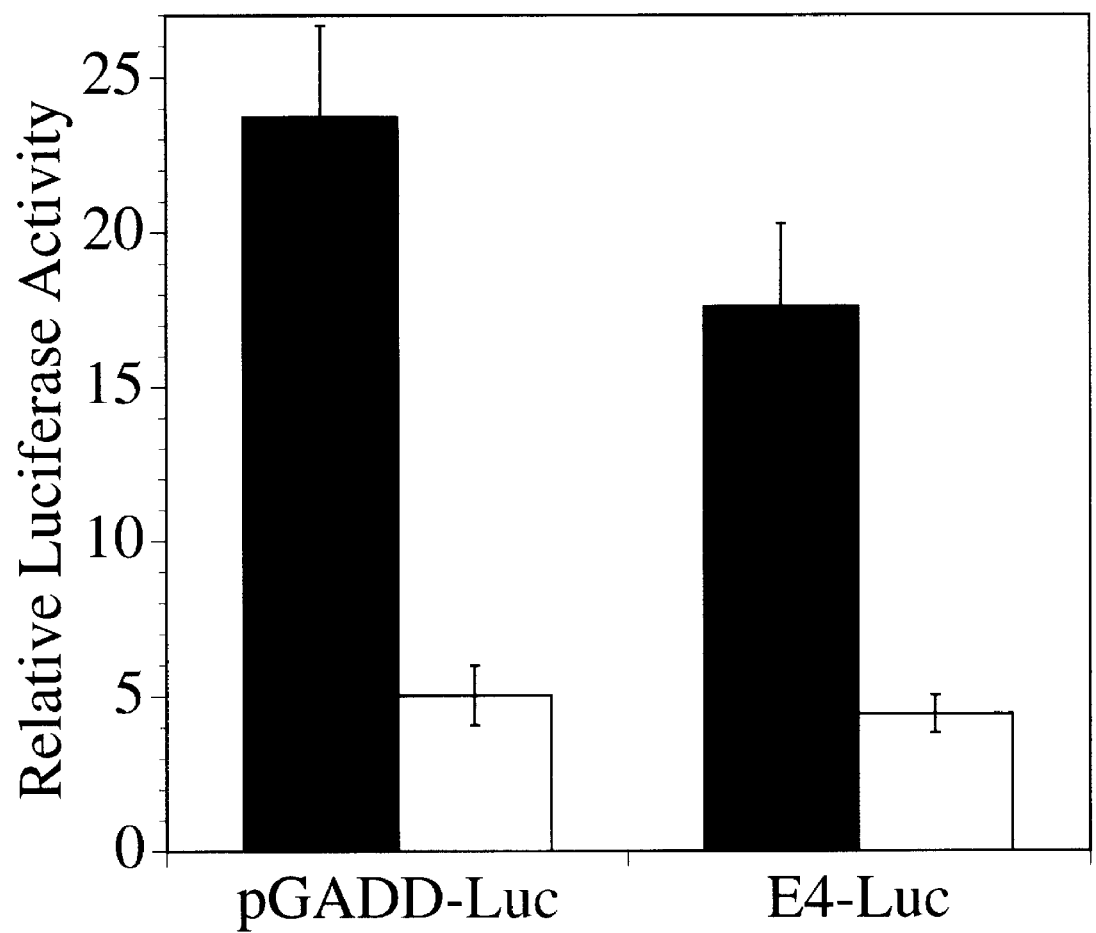
FIG. 3 shows the paclitaxel activation of the cellular injury response element placed upstream of a heterologous promoter. The cellular injury response element was placed 5′ of an adenovirus E4 early promoter TATA (−33 to +17 bases relative to the start of transcription) driven luciferase construct and lipofected into the 2008 cell line. The cells were treated with 70 nM paclitaxel and after 24 hours luciferase activity was assayed. The filled columns represent constructs containing the cellular injury response element and the TATA region, the empty columns represent constructs contain just the TATA region. Each column represents the mean of two experiments performed in duplicate ±SD.

In order to determine whether this 39 basepair sequence from −74 bases to the TATA box was sufficient to confer paclitaxel responsiveness to another promoter, these bases were transferred into a promoter containing the adenovirus E4-TATA region. The relative position of these 39 bases and the TATA box was kept constant. As shown in FIG. 3, the 39 bases conferred paclitaxel inducibility on the E4-TATA region, and the magnitude of induction was similar to that produced by the −74 GADD-LUC construct. This 39 base-pair region has been identified as a cellular injury response element (CIRE) The sequence of the CIRE SEQ. I.D. NO: 9 is:

AGG CTC CTG GGT CCC GCC CCC CAA AAG AGG GGA CGG GCC

The original sequence of the entire promoter is Luethy et al., *J Biol Chem*, 265(27) 16521–26 (1990).

EXAMPLE 11
Mutation of the Sp1 site within the CIRE

The cellular injury response element region from −74 to −35 contains only one known transcription factor recognition sequence, an Sp1 binding site. This site was mutated from CCCGCCCC to CCTAGACC using a PCR-based system and the activity of this construct was assayed. As shown at the bottom of FIG. 2, this mutation decreased the ability of paclitaxel to activate the promoter from 20.0-fold to 5.3-fold, indicating that the Sp1 site is a necessary part of the sequence that confers paclitaxel sensitivity.

EXAMPLE 12
Effect of paclitaxel on other Sp1-containing promoters

Figure 4:
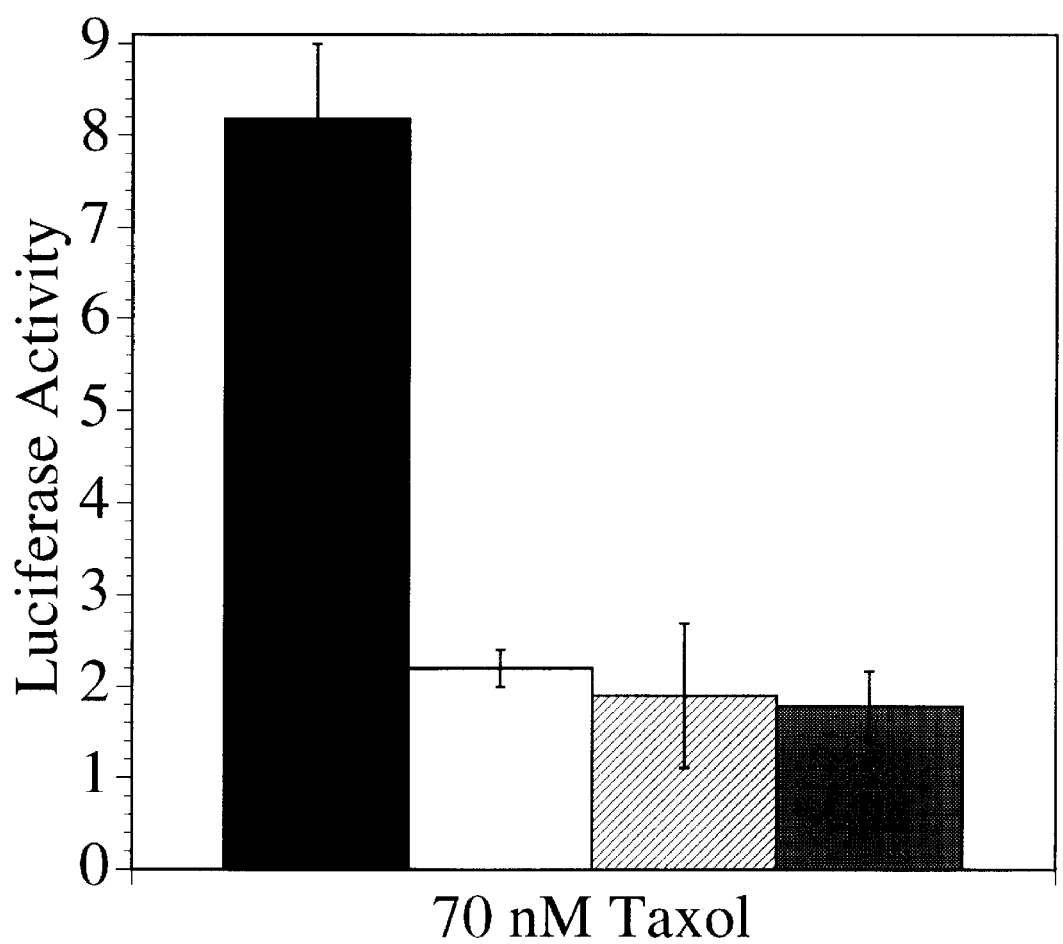
FIG. 4 shows the activation of other Sp1 containing promoters by 70 nM paclitaxel. Luciferase reporter constructs driven by the GADD153 promoter, the GADD153 TATA region, the SV40 early promoter, and the cytochrome p450 were lipofected into the 2008 cell line and treated with 70 nM paclitaxel. Luciferase activity was assayed after 24 hours. Each column represents the mean of three experiments performed in duplicate ±SD.

Since the Sp1 site appears to be required for the maximal paclitaxel-induced increase in promoter activity, whether paclitaxel activates all promoters which contained Sp1 sites was determined. This was explored using the SV40 immediate early promoter which contains 5 functional Sp1 sites and the cytochrome p450 CYP1A1 promoter which also contains 5 Sp1 sites (15). As shown in FIG. 4, paclitaxel increased the promoter activity in these constructs only 2-fold, which is the same increase as was observed in promoters containing only a TATA box. Thus, while an Sp1 site is required for paclitaxel activation, it is not sufficient and the exact positioning of the Sp1 site relative to the TATA box may be crucial.

EXAMPLE 13
DNAse I footprinting analysis of the GADD153 promoter

DNAse I protection assays were performed in order to determine which bases of the cellular injury response element are involved in the response to paclitaxel. The GADD153 promoter region from −185 to +21 bases relative to the start of transcription was $^{32}$P end-labeled and incubated with buffer alone or with 2 footprinting units of purified Sp1 protein, 10 $\mu$g nuclear extract from untreated cells, or 10 $\mu$g nuclear extract from cells treated with 70 nM paclitaxel for 24 hours.

Figure 5:
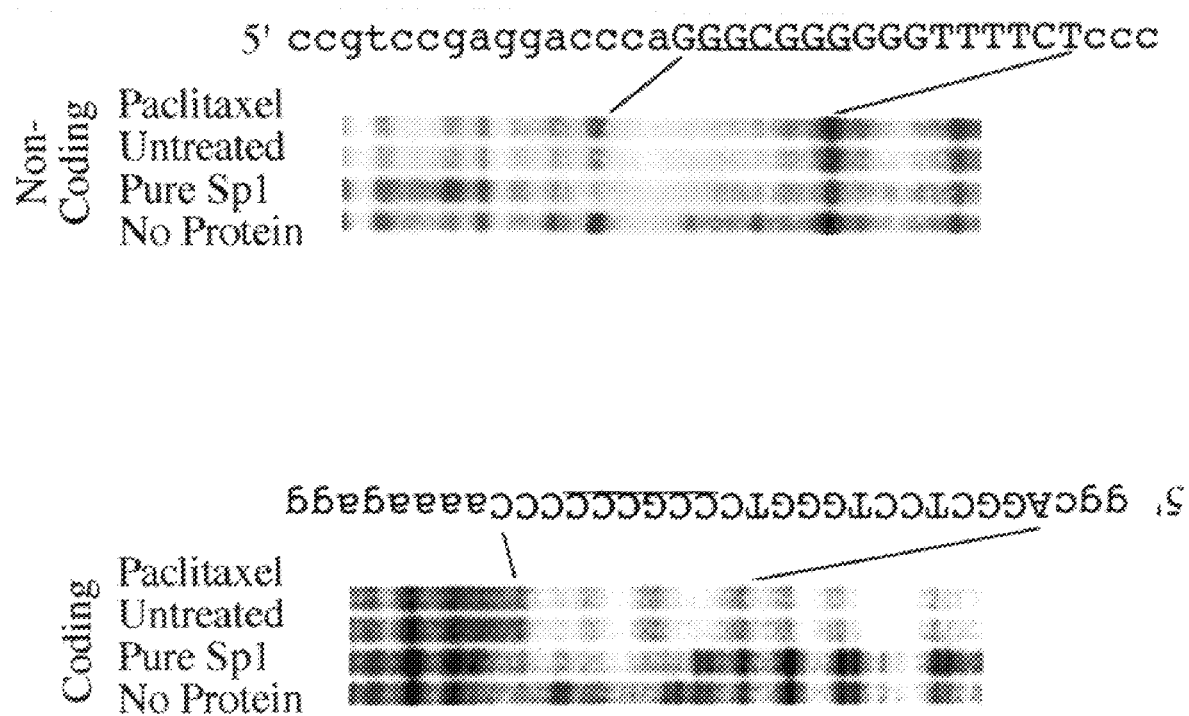
FIG. 5 shows the DNAse I footprinting of the cellular injury response element. The GADD153 promoter region from −185 to +21 bases relative to the start of transcription was labeled with $^{32}$P on either the coding SEQ. I.D. NO: 1. or non-coding SEQ. I.D. NO: 2 strand and incubated with buffer alone (No Protein), 2 footprinting units of purified Sp1 protein (Pure Sp1), 10 μg of nuclear extract from untreated cells (Untreated), or 10 μg nuclear extract from cells treated with 70 nM paclitaxel for 24 hours (Paclitaxel). The complex was incubated with DNAse I for 1 minute, the DNA was phenol/Chloroform extracted and separated on a 6% polyacrylamide/urea gel. Position was determined by dideoxy sequencing. Sp1 consensus site is underlined.

As shown in FIG. 5, the pure Sp1 and nuclear extracts from both untreated and treated cells protected the same region from −62 to −48 bases on the non-coding strand. The nuclear extracts protected from −74 to −53 on the coding strand; purified Sp1 had a similar pattern of protection, protecting bases −71 to −53. The region protected on both strands includes the Sp1 site which starts at −61 bases. This data suggests that Sp1, a protein complex which contains Sp1, or a protein that has the same binding characteristics as Sp1 is constitutively bound to the cellular injury response element.

Figure 6:
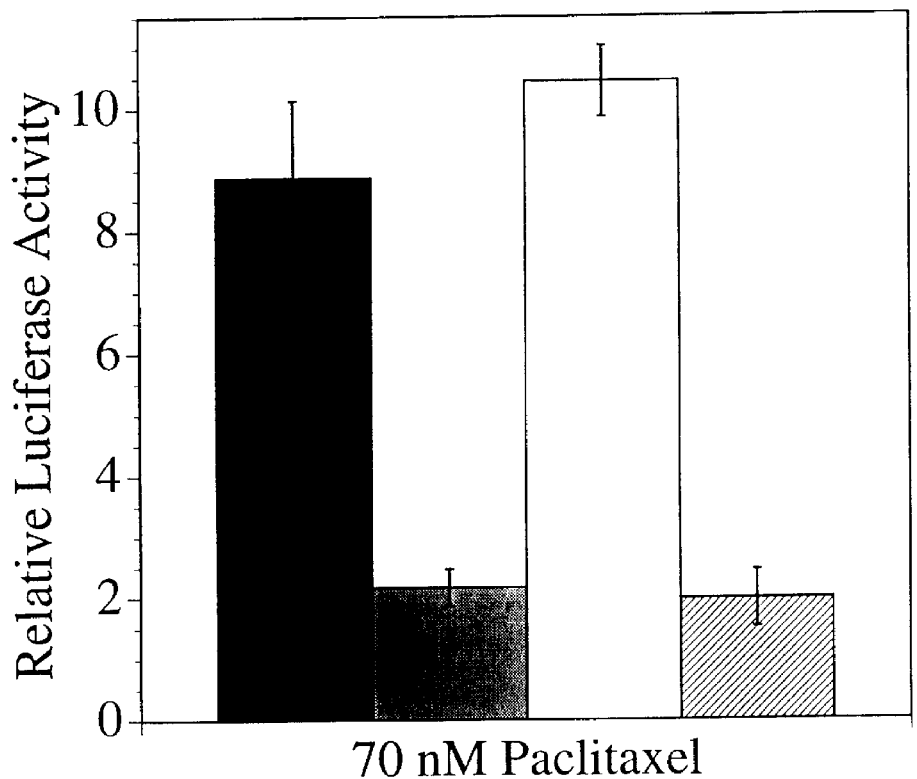
FIG. 6 shows the effect of linker scanning mutations on the paclitaxel activation of pGADD-LUC (−185). Linker scanning mutations of the region protected in the DNAse I footprinting assay were created by PCR. The mutated portions of the cellular injury response element are shown in FIG. 6A SEQ. I.D. NO: 1, SEQ. I.D. NO: 2 and SEQ. I.D. NO: 3. The capitalized bases were protected from DNAse I digestion by nuclear extracts, the Sp1 site is underlined and the mutations are in bold. The effect of these mutations are presented in FIG. 6B. The mutations were lipofected into the 2008 cell line, the cells were treated with 70 nM paclitaxel and luciferase activity was assayed after 24 hours. Each data point represents two experiments performed in duplicate ± SD.

EXAMPLE 14
Linker Scanning mutation of sites protected in footprinting assays In order to determine whether the sites protected in the DNAse protection assay are required for paclitaxel activation of the GADD 153 promoter or simply protected in a non-specific manner, the Sp1 site and the protected bases directly 3' of the Sp1 site were mutatedusing a linker scanning method. The sequence of the cellular injury response element and the mutations constructed are shown in the top panel of FIG. 6. As shown in the bottom panel of FIG. 6, mutations in the SP1 site decreased the inducibility of the construct to that of −35 pGADD-LUC which contains only the TATA box. Mutation of the site directly 3' of the Sp1 site had no significant effect on the activation of the promoter by paclitaxel. These data indicate that the Sp1 site, but not the protected site directly 3' of the Sp1 site, is required for activation of the GADD153 promoter by paclitaxel.

EXAMPLE 15
Gel Mobility Shift Assys

Figure 7:
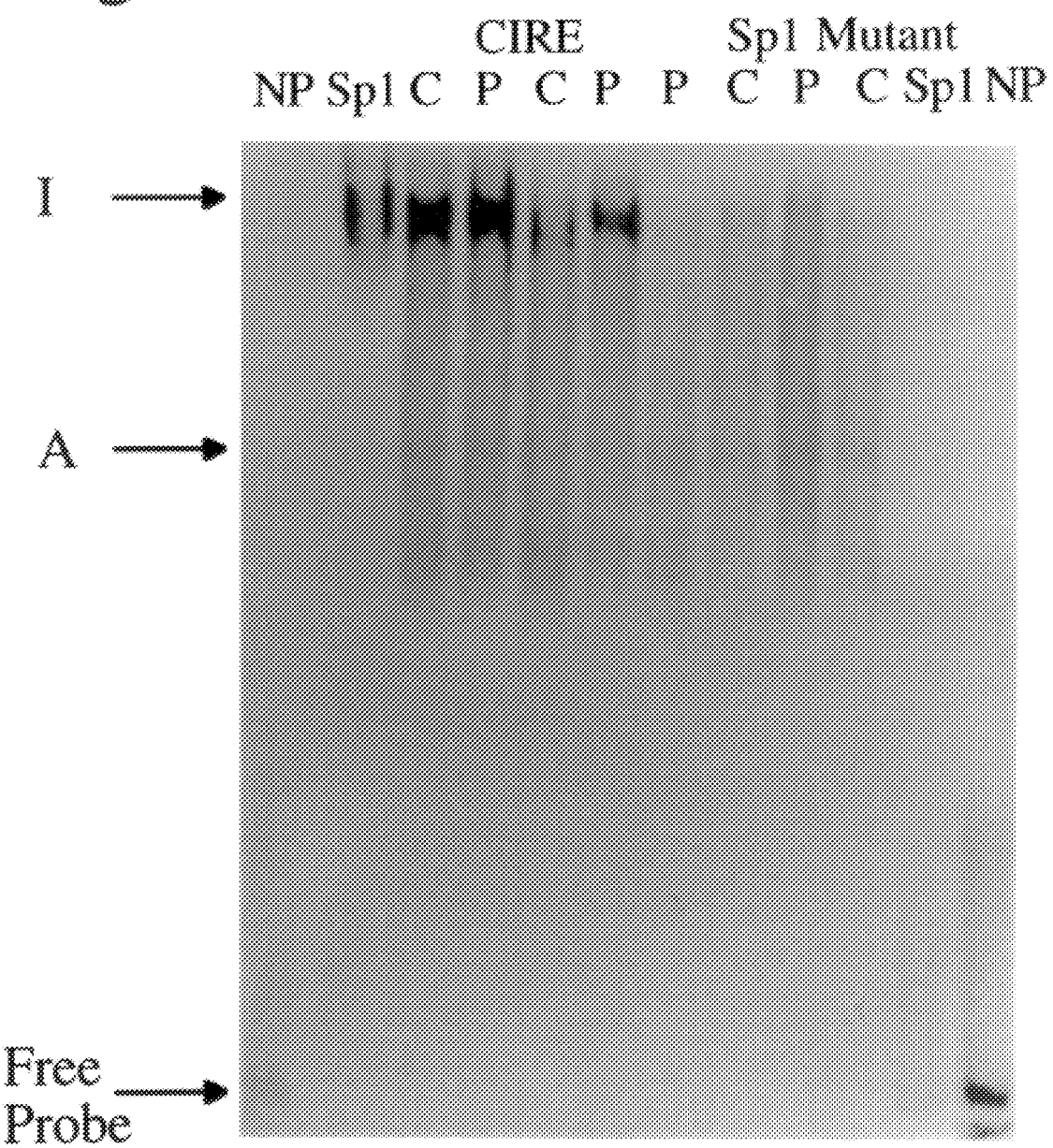
FIG. 7 shows the gel mobility shift assay of the cellular injury response element and CIRE-Sp1 mutant. The cellular injury response element (lanes 1–6) and the CIRE-Sp1 mutant (lanes 7–12) were end-labeled with $^{32}$P and incubated with no protein (lanes 1 & 7), purified Sp1 (lanes 2 & 8), nuclear extract form untreated cells (lanes 3, 4, 9&10), or nuclear extract from paclitaxel treated cells (lanes 5, 6, 11&12) before separation on a 4% polyacrylamide/0.5% TBE gel.

To further demonstrate the interaction between the cellular injury response element and nuclear proteins from untreated and paclitaxel-treated cells, a gel mobility shift assay was performed. Nuclear extracts were incubated with $^{32}$P-labeled cellular injury response element and separated on a 0.5X TBE/4% polyacrylamide gel. As shown in FIG. 7, 5 $\mu$g and 10 $\mu$g of nuclear extracts from untreated or paclitaxel-treated cells shifted the cellular injury response element to the same extent as purified Sp1 protein (labeled I, lanes 2–6). However, no shift was observed when nuclear extracts were incubated with the Sp 1-mutant cellular injury response element (labeled A in FIGS. 7 and 8; a non-specifically shifted band is labeled A in both FIGS. 7 and 8). Thus, the binding of the protein responsible for the gel shift of the cellular injury response element is dependent upon the presence of functional Sp1 site within the cellular injury response element.

Figure 8:
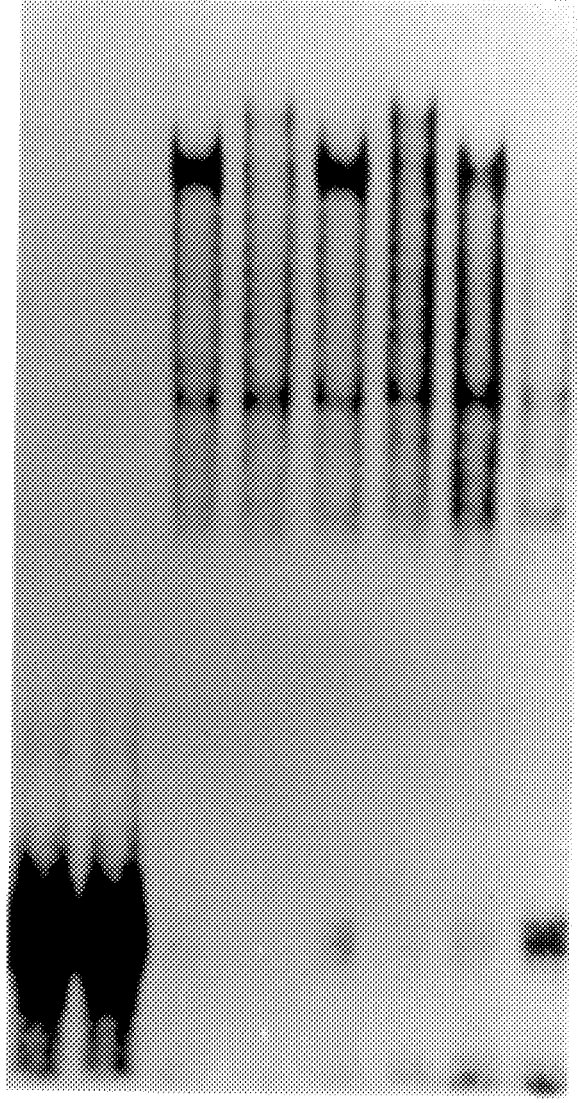
FIG. 8 shows the Sp1 supershift and gel mobility shift assays of the cellular injury response element using nuclear extracts immunodepleted of Sp1. The cellular injury response element was end-labeled with $^{32}$P as above and incubated with no protein (lane 1 and 2), nuclear extract form untreated cells (lanes 3 and 4), or nuclear extract from paclitaxel treated cells (lanes 5 and 6), and with non-specific rabbit antibody (lanes 1, 3 and 5) or rabbit α-Sp1 antibody (lanes 2, 4 and 6). The cellular injury response element was also incubated with mock depleted nuclear extract (lane 7) and Sp1-depleted nuclear extract (lane 8).

Since the shift in apparent molecular mass was dependent upon a functional Sp1 site, it was determined whether Sp1 was bound to the cellular injury response element after incubation with nuclear extract. As shown in FIG. 8, co-incubation of the nuclear extract-exposed cellular injury response element with a rabbit polyclonal antibody raised against amino acids 520–538 of human SP1 protein (PEP2) caused a supershift and increased the apparent molecular weight of the shifted complex (labeled II, lanes 4 and 6), whereas non-specific rabbit antibody had no effect on the mobility of the complex (labeled I, lanes 3 and 5). This indicates that Sp1 protein is part of the complex which shifts the cellular injury response element.

To determine whether Sp1 protein is required for the formation of the complex that shifts the cellular injury response element, Sp1 was immunodepleted from the nuclear extract with the PEP2 anti-Sp1 antibody. The mock depleted extract shifted the cellular injury response element to the same extent as the untreated nuclear extract (lane 7). However, immunodepletion of Sp1 abolished the shift (lane 8). Thus, Sp1 protein is required for formation of the complex that shifts the cellular injury response element.

The present invention demonstrates that treatment of human ovarian carcinoma cells with the chemotherapeutic drug paclitaxel activates the GADD153 promoter through an element of no larger than 39 bases positioned immediately 5' of the TATA box that has been identified as a cellular injury response element (CIRE). Three lines of evidence establish that the cellular injury response element of the present invention is necessary and sufficient for transcription activation of this promoter. First, deletion of the cellular injury response element eliminates the ability of paclitaxel to activate the GADD153 promoter above the level observed with a promoter containing only the TATA box. Secondly, mutation of the key Sp1 site within this element inhibits the ability of paclitaxel to activate the promoter. Thirdly, transfer of the cellular injury response element to a position 5' of a heterologus promoter confers paclitaxel induceability.

Work by Sylvester et al. suggested that transcriptional activation of the GADD153 promoter after treatment with lipopolysaccharide required the binding of transcription factors to the C/EBP element present in the promoter at −332 to −323 bases relative to the start of transcription (15). However, this element does not appear to be involved in the cellular response to paclitaxel. This data is consistent with the showing that induction of GADD153 can be mediated by several pathways that differ depending on the type of growth inhibitory stimulus (9,16).

The cellular injury response element that mediates transcriptional activation by paclitaxel contains an Sp1 consensus sequence (CCCGCC) at −61 bases relative to the start of transcription. As shown by the direct mutation and linker scanning mutations, this site is required for activation of the promoter by paclitaxel, whereas the 3 other Sp1 sites further 5' in this promoter apparently are not required and cannot substitute for the Sp1 site in the cellular injury response element. The specificity of the Sp1 site in the cellular injury response element is further demonstrated by the fact that paclitaxel does not activate the SV40 early promoter, demonstrating that Sp1 sites alone are not sufficient for full activation. The results provide strong evidence that the transcription factor responsible for the activation of the GADD153 promoter by paclitaxel is Sp1 or a very closely related protein. In DNAse I protection assays, the footprint of purified Sp1 is similar to that of the nuclear extract in that region of the promoter. A protein or proteins present in the nuclear extract binds to the cellular injury response element and shifts the DNA to the same extent as purified Sp1 protein, but cannot shift the cellular injury response element containing a mutation in the Sp1 site. An antibody specific for Sp1 supershifted the nuclear extract/cellular injury response element complex, indicating that Sp1 is part of the complex. Sp1 is required for this binding since immunodepletion of Sp1 from the nuclear extract abolished the gel shift. These experiments very strongly suggest that Sp1 is the protein which binds to the cellular injury response element. There is a small possibility that a protein which cross-reacts with the Sp1 antibody is the protein that binds to the cellular injury response element. Recent evidence suggests that there is a family of proteins which can bind to the Sp1 consensus site (17–20), however, the fact that the PEP2 anti-Sp1 antibody is highly specific and does not crossreact with other family members makes it unlikely that another known member of the family is involved.

While Sp1 was originally thought to be a ubiquitous transcription factor involved solely in the constitutive expression of genes (21), recent evidence suggests that Sp1 is critical for regulated expression in some situations. Sp1 can act in concert with a cell type-specific protein in order to achieve tissue-specific expression. Both Sp1 and the sterol regulatory binding protein I are required for normal sterol-mediated regulation of the low density lipoprotein receptor promoter (22). This regulatory strategy is also utilized in the TF-1 erythroleukemia cell line. In this system, Sp1 complexes with p53 after granulocyte/macrophage colony stimulating factor stimulation, and this results in increased binding of Sp1 to its consensus sequences without a change in total Sp1 protein level (23,24). As a third example of the involvement of Sp1 in tissue-specific transcription, linker scanning mutations of the myeloid integrin CD11b promoter demonstrated that mutation of the Sp1 site abolished myeloid-specific promoter activity (25). Interestingly, using in vitro footprinting, Sp1 was found bound to this consensus sequence in both HeLa and myleoid cells, but the Sp1 site was only protected in in vivo footprints in the myleoid cell line. This group has also demonstrated similar findings in a monocyte cell line. Mutation of the Sp1 site in the moncytic marker gene CD14 decreased the activity of the promoter in monocytes, yet had only minor effects on the activity in HeLa cells (26). Thus, there are now several examples of transcriptional activation of promoters where Sp1 is an essential component but nevertheless is involved in regulated rather than constitutive expression.

Despite the evidence that the Sp1 binding site in the cellular injury response element is essential for paclitaxel-induced activation of the GADD153 promoter, paclitaxel did not produce a change in apparent Sp1 binding to this consensus sequence. Sp1 was present in complexes formed with the paclitaxel cellular injury response element by nuclear extracts from both untreated and paclitaxel-exposed cells, and a footprint consistent with Sp1 was produced in in vitro DNAse I protection by nuclear extracts from both types of cells. However, there is evidence of such constitutive binding in several other Sp1-dependent inducible systems. The retinoblastoma protein regulates the expression of a number of genes including c-fos, c-jun, c-myc, IGF-II and TGF 1 through a retinoblastoma control element (RCE) (27,28). Sp1 protein binds to the RCE consitutively in the IGF-II and the c-jun promoters (27,28). The amount of this binding is increased in the c-jun promoter in response to Rb expression, possibly through the interaction of RB protein and an inhibitor of Sp1 binding (Sp1-I) (28), but no change in binding of Sp1 as measured by gel shift or DNAse I footprinting was observed in the IGF-II promoter following Rb expression (27).

Apparently, in the case of the GADD153 promoter, formation of the complex for which the Sp1 site is essential and which contains Sp1 is not by itself sufficient for activation of the promoter suggesting that activation requires additional events such as phosphorylation of either Sp1 itself or one of the TAFs with which it associates. Recent data suggests that paclitaxel can activate a number of protein kinases (29–32). Paclitaxel has been shown to cause an increase in the release of TNF and an upregulation of the TNF receptor in macrophages (31). This effect was absent in mice that are hyporesponsive to bacterial LPS, suggesting that paclitaxel and LPS are acting on the same effector. It was later found that paclitaxel and LPS activate the same genes in macrophages, possibly through tyrosine phosphorylation of 41 and 42 kD proteins (32). Liu et al. have documented that paclitaxel kills cells via induction of apoptosis (30), and that during the apoptotic response there is a decrease in the inhibitor bcl-2. The increase in apoptosis and the decrease in bcl-2 expression could be blocked by genistein or herbamycin, suggesting that paclitaxel is exerting these effects via a tyrosine kinase. Haldar and Croce have demonstrated that paclitaxel treatment phosphorylates and inactivates bcl-2, therefore activating the apoptotic response (29). A 24 hour treatment with 100 nM paclitaxel increases the phosphorylation of histone H3 (data not shown). Thus, paclitaxel treatment activates a number of different kinase that could be responsible for the activation of transcription from Sp1 constitutively bound to DNA.

There is also evidence that phosphorylation of Sp1 can alter its transcriptional activity. Okadaic acid stimulates the HIV LTR through Sp1 sites, yet the binding characteristics of Sp1 to the promoter are unchanged (33). Using Western blotting, it was observed that okadaic acid treatment resulted in the complete conversion of Sp1 from the hypophosphorylated state (95 kD) to the hyperphosphorylated state (105 kD). In order to determine whether Sp1 phosphorylation induced changes in the interaction with TBP or TBP-associated proteins (TAFs), the TATA box was exchanged with a non-TBP binding TATA box. This change strongly decreased the induceability by okadaic acid. The authors postulated that phosphorylation of Sp1 increases interaction with TBP or TAFs, which results in increased transcriptional activity.

It is likely that Sp1 is constitutively bound to the Sp1 site at −61 bases relative to the start of transcription, and that after paclitaxel treatment a post-translation modification occurs which allows the Sp1 to activate transcription. Since paclitaxel treatment did not alter the phosphorylation-dependent electrophoretic mobility of Sp1 (data not shown), it is likely that if phosphorylation is involved, it is one of the TAFs that is the essential target. Alternatively, activation may be the result of a change in the distribution of phosphorylated sites within Sp1 that does not change the electrophoretic mobility of Sp1. This change in phosphorylation would allow a TAF which interacts with Sp1, such as TAFII110 (34), to bind to both Sp1 and the TATA-binding protein and initiate transcription. An alternative explanation is that paclitaxel treatment has no effect on Sp1 protein, but modifies TAFII110 or another of the TAFs in such a way that they can bind to Sp1 and TBP and increase transcription. As with other observations suggesting that Sp1 can act as a transcription factor for inducible genes, it is not known why transcriptional activation can occur from one Sp1 site but not from other Sp1 sites in the same promoter. The Sp1 site at −61 in the GADD153 promoter has some special features the elucidation of which will help solve this puzzle.

THE FOLLOWING REFERENCES WERE CITED HEREIN

1. Holbrook, N. J., and Fornace, A. J. (1991) The New Biologist 3(9), 825–833
2. El-Deiry, W. S., Tokino, T., Velculescu, V. E., Levy, D. B., Parsons, R., Trent, J. M., Lin, D., Mercer, W. E., Kinzer, K. W., and Vogelstein, B. (1993) Cell 75, 817–825
3. Kastan, M. B., Zhan, Q., El-Diery, W. S., Carrier, F., Jacks, T., Walsh, W. V., Plankett, B. S., Vogelstein, B., and Fornace, A. J. (1992) Cell 71, 587–597
4. Fornace, A. J., Alamo, I., and Hollander, M. C. (1988) Proceedings of the National Academy of Sciences, USA 85, 8800–8804
5. Fornace, A. J., Nebert, D. W., Hollander, C., Luethy, J. D., Papathanasiou, M., Fargnoli, J., and Holbrook, N. (1989) Molecular and Cellular Biology 9(10), 4196–4203
6. Park, J. S., Luethy, J. D., Wang, M. G., Fargnoli, J., Fornace, A. J., McBride, O. W., and Holbrook, N. J. (1992) Gene 116, 259–267
7. Zhan, Q., Lord, K. D., Alamo, I., Hollander, M. C., Carrier, F., Ron, D., Kohn, K. W., Hoffman, B., Liebermann, D. A., and Fornace, A. J. (1994) Molecular and Cellular Biology 14(4), 2361–2371
8. Barone, M. V., Crozat, A., Tabaee, A., Philipson, L., and Ron, D. (1994) Genes and Development 8, 453–464
9. Gately, D. P., Sharma, A., Christen, R. D., and Howell, S. B. (1996) British Journal of Cancer, 73 (1), 8–23.
10. DiSaia, P. J., Sinkovics, J. G., Rutledge, F. N., and Smith, J. P. (1972) American Journal of Obstetric Gynecology 114, 979–989
11. Luethy, J. D., and Holbrook, N. J. (1992) Cancer Research 52, 5–10
12. Rose, J. K., Buonocore, L., and Whitt, M. A. (1991) BioTechniques 10(4), 520–525
13. Brasier, A. R., Tate, J. E., and Habener, J. F. (1989) BioTechniques 7(10), 1116–1122
14. Davis, L. G., Dibner, M. D., and Battey, J. F. (1986) Basic methods in molecular biology, Elsevier Science Publishing Co. Inc., New York, NY
15. Sylvester, S. L., ap Rhys, C. M. J., Leuthy-Martindale, J. D., and Holbrook, N. J. (1994) The Journal of Biological Chemistry 269(31), 20119–20125
16. Jackman, J., Alamo, I., and Fornace, A. J. (1994) Cancer Research 54, 5656–5662
17. Majello, B., De Luca, P., Hagen, G., Suske, G., and Lania, L. (1994) Nucleic Acids Research 22(23), 4914–4921
18. Hagen, G., Müller, S., Beato, M., and Suske, G. (1994) The EMBO Journal 13(16), 3843–3851
19. Kingsley, C., and Winoto, A. (1992) Molecular and Cellular Biology 12(10), 4251–4261
20. Hagen, G., Müller, S., Beato, M., and Sucke, G. (1992) Nucleic Acids Research 20(21), 5519–5525
21. Briggs, M. R., Kadonaga, J. T., Bell, S. P., and Tjian, R. (1986) Science 234, 47–52
22. Yieh, L., Sanchez, H. B., and Osborne, T. F. (1995) PNAS 92, 6102–6106
23. Borellini, F., Aquino, A., Josephs, S. F., and Glazer, R. I. (1990) Molecular and Cellular Biology 10(10), 5541–5547
24. Borellini, F., and Glazer, R. I. (1993) The Journal of Biological Chemistry 268(11), 7923–7928
25. Chen, H.-M., Pahl, H. L., Scheibe, R. J., Zhang, D. -E., and Tenen, D. G. (1993) The Journal of Biological Chemistry 268(11), 8230–8239
26. Zhang, D. -E., Hetherington, C. J., Tan, S., Dziennis, S. E., Gonzalez, D. A., Chen, H.-M., and Tene, D. G. (1994) the Journal of Biological Chemistry 269(15), 11425–11434
27. Kim, S. -J., Onwuta, U. S., Lee, Y. I., Li, R., Botchan, M. R., and Robbins, P. D. (1992) Molecular and Cellular Biology 12(6), 2455–2463
28. Chen, L. I., Nishinaka, T., Kwan, K., Kitabayashi, I., Yokoyama, K., Fu, Y. -H. K., Grünwald, S., and Chiu, R. (1994) Molecular and Cellular Biology 14(7), 4380–4389
29. Haldar, S., Jena, N., and Croce, C. M. (1995) The Journal of Biological Chemistry 92, 4507–4511
30. Liu, Y., Bhalla, K., Hill, C., and Priest, D. G. (1994) Biochemical Pharmacology 48(6), 1265–1272
31. Ding, A. H., Porteu, F., Sanchez, E., and Nathan, C. F. (1990) Science 248, 370–372
32. Manthey, C. L., Brandes, M. E., Perera, P. Y., and Vogel, S. N. (1992) The Journal of Immunology 149(7), 2459–2465
33. Vlach, J., Garcia, A., Jacqué, J. -M., Rodriguez, M. S., Michelson, S., and Virelizier, J. -L. (1995) Virology 208, 753–761
34. Gill, G., Pascal, E., Tseng, Z. H., and Tjian, R. (1994) PNAS, 91, 192–196

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A vector comprising a DNA sequence coding for a cellular injury response element promoter, said promoter having nucleotides −74 to −35 of the GADD153 promoter, relative to the start of transcription, in operable linkage:

a) an origin of replication;

b) a promoter; and c) a DNA sequence coding for said promoter.

2. The vector of claim 1, wherein said vector is selected from the group consisting of a retroviral vector, an adenoviral vector, an adeno-associated vector and a plasmid.

3. The vector of claim 1, wherein said promoter has the sequence shown in SEQ ID NO: 9.

4. The vector of claim 1, wherein said DNA sequence coding for a cellular injury response element promoter is linked to a reporter gene.

5. The vector of claim 1, wherein said DNA sequence coding for a cellular injury response element promoter is linked to a gene coding for a protein selected from the group consisting of a secreted hormone, growth factor, cytokine and, chemokine.

6. The vector of claim 1, wherein said protein is selected from the group consisting of insulin, G-CSF and thrombopoeitin.

7. The vector of claim 1, wherein said DNA sequence coding for a cellular injury response element promoter is linked to a gene coding for a transcription factor.

8. The vector of claim 1, wherein said DNA sequence coding for a cellular injury response element promoter is linked to a gene coding for melanin.

9. The vector of claim 1, wherein said DNA sequence coding for a cellular injury response element promoter is linked to a gene coding for a cell surface receptor.

10. The vector of claim 1, wherein said DNA sequence coding for a cellular injury response element promoter is linked to a gene coding for an intracellular receptor.

11. The vector of claim 1, wherein said DNA sequence coding for a cellular injury response element promoter is linked to a toxin gene.

12. A host cell transfected with the vector of claim 1, said vector expressing a cellular injury response element promoter, said promoter having nucleotides −74 to −35 of the GADD153 promoter, relative to the start of transcription.

13. The host cell of claim 12, wherein said cell is selected from group consisting of bacterial cells, mammalian cells and insect cells.

14. The vector of claim 9, wherein said cell surface receptor is the epidermal growth factor receptor.

15. The vector of claim 10, wherein said intracellular receptor is a steroid hormone receptor.

16. The vector of claim 11, wherein said toxin gene is selected from the group consisting of gelonin, ricin and saponin.

* * * * *

UNITED STATES PATENT AND TRADEMARK OFFICE
CERTIFICATE OF CORRECTION

PATENT NO. : 5,770,430
DATED : June 23, 1998
INVENTOR(S) : Stephen B. Howell and Dennis P. Gately It is certified that error appears in the above-identified patent and that said Letters Patent is hereby corrected as shown below:

Column 2, line 27, "indate" should read --indicate--.
Column 4, line 18, "contain" should read --containing--.
Column 4, line 61, "form"should read --from--.
Column 5, line 28, "acid" should read --acids--.
Column 5, line 36, "nomeclature" should read --nomenclature--.
Column 8, line 16, please remove the apostrophe after the word " heterologous" and replace with end quotation marks.
Column 8, line 54, "quantitiy" should read --quantity--.
Column 9, line 13, "gorwth" should read --growth--.
Column 11, line 47, "expeosed" should read --exposed--.
Column 12, line 31, "expeosed" should read --exposed--.
Column 13, line 3, please insert a period after the word "(CIRE)".
Column 16, line 23, "consitutively" should read --constitutively--.

Signed and Sealed this

Ninth Day of January, 2001

*Attest:*

Q. TODD DICKINSON

*Attesting Officer*  *Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 34
( B ) TYPE: nucleic acid
( C ) STRANDEDNESS: double
( D ) TOPOLOGY: linear ( i i ) MOLECULE TYPE:
( A ) DESCRIPTION: other nucleic acid ( i i i ) HYPOTHETICAL: No ( i v ) ANTI-SENSE: No ( v i ) ORIGINAL SOURCE:
( B ) STRAIN:
( C ) INDIVIDUAL ISOLATE:
( D ) DEVELOPMENTAL STAGE:
( F ) TISSUE TYPE:
( G ) CELL TYPE:
( H ) CELL LINE:

( x i ) SEQUENCE DESCRIPTION: SEQ ID NO:1:

GGCAGGCTCC TGGGTCCCGC CCCCCAAAAG AGGG 34

( 2 ) INFORMATION FOR SEQ ID NO:2:

( i ) SEQUENCE CHARACTERISTICS:
( A ) LENGTH: 34
( B ) TYPE: nucleic acid
( C ) STRANDEDNESS: double
( D ) TOPOLOGY: linear ( i i ) MOLECULE TYPE:
( A ) DESCRIPTION: other nucleic acid ( i i i ) HYPOTHETICAL: No ( i v ) ANTI-SENSE: No ( v i ) ORIGINAL SOURCE:
( B ) STRAIN:
( C ) INDIVIDUAL ISOLATE:
( D ) DEVELOPMENTAL STAGE:
( F ) TISSUE TYPE:
( G ) CELL TYPE:
( H ) CELL LINE:

( x i ) SEQUENCE DESCRIPTION: SEQ ID NO:2:

CCGTCCGAGG ACCCAGGGCG GGGGGTTTTC TCCC 34

( 2 ) INFORMATION FOR SEQ ID NO:3:

( i ) SEQUENCE CHARACTERISTICS:
( A ) LENGTH: 34
( B ) TYPE: nucleic acid
( C ) STRANDEDNESS: double
( D ) TOPOLOGY: linear ( i i ) MOLECULE TYPE:
( A ) DESCRIPTION: other nucleic acid ( i i i ) HYPOTHETICAL: No ( i v ) ANTI-SENSE: No ( v i ) ORIGINAL SOURCE:

(B) STRAIN:
(C) INDIVIDUAL ISOLATE:
(D) DEVELOPMENTAL STAGE:
(F) TISSUE TYPE:
(G) CELL TYPE:
(H) CELL LINE:

(x i) SEQUENCE DESCRIPTION: SEQ ID NO:3:

GGCAGGCTCC TGGGTCCCGC CCCCCAAAAG AGGG 34

(2) INFORMATION FOR SEQ ID NO:4:

(i) SEQUENCE CHARACTERISTICS:
        (A) LENGTH: 34
        (B) TYPE: nucleic acid
        (C) STRANDEDNESS: double
        (D) TOPOLOGY: linear (i i) MOLECULE TYPE:
        (A) DESCRIPTION: other nucleic acid (i i i) HYPOTHETICAL: No (i v) ANTI-SENSE: No (v i) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(x i) SEQUENCE DESCRIPTION: SEQ ID NO:4:

CCGTCCGAGG ACCCAGGGCG GGGGGTTTTC TCCC 34

(2) INFORMATION FOR SEQ ID NO:5:

(i) SEQUENCE CHARACTERISTICS:
        (A) LENGTH: 34
        (B) TYPE: nucleic acid
        (C) STRANDEDNESS: double
        (D) TOPOLOGY: linear (i i) MOLECULE TYPE:
        (A) DESCRIPTION: other nucleic acid (i i i) HYPOTHETICAL: No (i v) ANTI-SENSE: No (v i) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(x i) SEQUENCE DESCRIPTION: SEQ ID NO:5:

GGCAGGCTCC TGGGTCCCTA GACCCAAAAG AGGG 34

(2) INFORMATION FOR SEQ ID NO:6:

(i) SEQUENCE CHARACTERISTICS:
        (A) LENGTH: 34
        (B) TYPE: nucleic acid
        (C) STRANDEDNESS: double
        (D) TOPOLOGY: linear (i i) MOLECULE TYPE:
        (A) DESCRIPTION: other nucleic acid (i i i) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:6:

CCGTCCGAGG ACCCAGGGAT CTGGGTTTTC TCCC    34

( 2 ) INFORMATION FOR SEQ ID NO:7:

( i ) SEQUENCE CHARACTERISTICS:
    ( A ) LENGTH: 34
    ( B ) TYPE: nucleic acid
    ( C ) STRANDEDNESS: double
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:7:

GGCAGGCTCC TGGGTCCCGC CCCCTCTCT AGGG    34

( 2 ) INFORMATION FOR SEQ ID NO:8:

( i ) SEQUENCE CHARACTERISTICS:
    ( A ) LENGTH: 34
    ( B ) TYPE: nucleic acid
    ( C ) STRANDEDNESS: double
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:8:

CCGTCCGAGG ACCCAGGGCG GGGGAGAGA TCCC    34

( 2 ) INFORMATION FOR SEQ ID NO:9:

( i ) SEQUENCE CHARACTERISTICS:
    ( A ) LENGTH: 39
    ( B ) TYPE: nucleic acid
    ( C ) STRANDEDNESS: double
    ( D ) TOPOLOGY: linear (ii) MOLECULE TYPE:
            (A) DESCRIPTION: other nucleic acid (iii) HYPOTHETICAL: No (iv) ANTI-SENSE: No (vi) ORIGINAL SOURCE:
            (B) STRAIN:
            (C) INDIVIDUAL ISOLATE:
            (D) DEVELOPMENTAL STAGE:
            (F) TISSUE TYPE:
            (G) CELL TYPE:
            (H) CELL LINE:

(xi) SEQUENCE DESCRIPTION: SEQ ID NO:9:

AGG CTC CTG GGT CCC GCC CCC CAA AAG AGG GGA CGG GCC        39